(12) United States Patent
Saleh et al.

(10) Patent No.: US 8,232,509 B2
(45) Date of Patent: Jul. 31, 2012

(54) RETAINER SYSTEM

(75) Inventors: Saleh A. Saleh, Vernon Hills, IL (US);
Andrea Pedrotti, Cavedine, TN (US);
Walter Sordo, Trento (IT)

(73) Assignee: S.C. Johnson & Son, Inc., Racine, WI (US)

( * ) Notice: Subject to any disclaimer, the term of this patent is extended or adjusted under 35 U.S.C. 154(b) by 1136 days.

(21) Appl. No.: 11/560,577

(22) Filed: Nov. 16, 2006

(65) Prior Publication Data

US 2008/0117018 A1    May 22, 2008

(51) Int. Cl.
*H05B 3/06* (2006.01)
*H05B 1/02* (2006.01)
*H05B 3/58* (2006.01)
*H01C 7/10* (2006.01)
*H01C 7/13* (2006.01)

(52) U.S. Cl. ........ 219/520; 219/505; 219/517; 219/535; 338/22 R

(58) Field of Classification Search .................. 219/520, 219/535, 517, 536, 505; 392/395; 338/315, 338/316, 226, 273, 276, 22 R, 202, 212
See application file for complete search history.

(56) References Cited

U.S. PATENT DOCUMENTS

| | | | | |
|---|---|---|---|---|
| 2,866,054 A | * | 12/1958 | Purdy | 338/174 |
| 2,999,993 A | * | 9/1961 | Sherwood | 338/176 |
| 3,264,594 A | * | 8/1966 | Layland | 338/174 |
| 3,533,042 A | * | 10/1970 | Casey et al. | 338/162 |
| 3,806,323 A | | 4/1974 | Thompson | |
| 3,861,880 A | | 1/1975 | Thompson | |
| 4,037,082 A | * | 7/1977 | Tamada et al. | 219/541 |
| 4,251,714 A | * | 2/1981 | Zobele | 392/392 |
| 4,286,754 A | | 9/1981 | Jones | |
| 4,439,415 A | | 3/1984 | Hennart et al. | |
| 4,635,026 A | * | 1/1987 | Takeuchi | 338/22 SD |
| 4,728,779 A | * | 3/1988 | Kotani et al. | 219/517 |
| 4,814,584 A | * | 3/1989 | Bohlender et al. | 219/535 |
| 4,822,572 A | | 4/1989 | Van der Smissen et al. | |
| 4,874,924 A | * | 10/1989 | Yamamoto et al. | 392/395 |
| 5,262,619 A | * | 11/1993 | Karner | 392/485 |
| 5,431,885 A | | 7/1995 | Zlotnik et al. | |
| 5,948,424 A | | 9/1999 | Kandathil et al. | |
| 6,192,169 B1 | * | 2/2001 | Cammons et al. | 385/14 |
| 6,374,045 B2 | * | 4/2002 | Basaganas Millan | 392/395 |
| 6,411,776 B1 | * | 6/2002 | Millan | 392/395 |

(Continued)

FOREIGN PATENT DOCUMENTS

EP   0290159 B1   12/1994

(Continued)

*Primary Examiner* — Henry Yuen
*Assistant Examiner* — Hemant Mathew

(57) ABSTRACT

The invention provides a retainer system for retaining a positive temperature coefficient resistor in a heater housing shaft having a shaft side wall. The retainer system includes a base, a spring, and shaft engagement means. The spring is formed in and spaced apart from the base. The spring extends radially outwardly from a longitudinal axis of the base and the spring has a neck that curves radially backwardly, spaced apart from the base and toward the longitudinal axis of the base. The spring also has a contact surface presented outwardly, away from the base. The shaft engagement means are for engaging the shaft side wall and securing the base within the shaft at a desired distance from the resistor. The retainer system can be secured within the shaft with the spring flexed to a desired extent and with the contact surface urged against the resistor to retain the resistor in the shaft.

16 Claims, 9 Drawing Sheets

U.S. PATENT DOCUMENTS

| | | |
|---|---|---|
| 6,551,560 B1 | 4/2003 | Flashinski et al. |
| 6,581,915 B2 | 6/2003 | Bartsch et al. |
| 6,773,679 B2 | 8/2004 | Jaworski et al. |
| 6,813,886 B2 * | 11/2004 | Cerruti et al. ............... 60/527 |
| 6,834,847 B2 | 12/2004 | Bartsch et al. |
| 6,925,252 B2 | 8/2005 | Zhang et al. |
| 7,012,225 B2 * | 3/2006 | Bohlender et al. ............ 219/536 |
| 2002/0066798 A1 | 6/2002 | Laudamiel-Pellet et al. |
| 2004/0007787 A1 | 1/2004 | Kvietok et al. |
| 2004/0140114 A1 | 7/2004 | Wagner |
| 2004/0151747 A1 | 8/2004 | Davis et al. |
| 2005/0029901 A1 * | 2/2005 | Gadini et al. ................ 310/306 |
| 2005/0284952 A1 | 12/2005 | Davis et al. |

FOREIGN PATENT DOCUMENTS

| | | |
|---|---|---|
| EP | 0591537 B1 | 11/1996 |
| EP | 965267 A1 * | 12/1999 |
| EP | 965267 B1 | 12/1999 |
| WO | WO 97/02054 | 1/1997 |
| WO | WO 9702054 A1 * | 1/1997 |
| WO | WO 97/45008 | 12/1997 |
| WO | WO 98/57674 | 12/1998 |
| WO | WO 2006/046209 | 5/2006 |

* cited by examiner

RETAINER SYSTEM

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

1. Field of the Invention

The retainer system of the invention relates to electrical heater devices that employ positive temperature coefficient resistors ("PTC resistors") and the means and methods of securing PTC resistors within such heater devices.

2. Description of the Related Art

PTC resistors are well known in the art and are frequently used in small electrical heater devices. Examples of such electrical heater devices are small heaters designed to dispense volatiles into the air. Such volatiles include scents, insect control active ingredients, and the like. For example, WO 2006/046209 discloses a form of positive temperature coefficient electric heating device for vaporizing insecticides and fragrances impregnated in a solid mat. A variety of heating elements have been developed for these and analogous applications. See generally U.S. Pat. Nos. 4,037,082, 4,251,714, 4,635,026, 4,728,779, 4,814,584, 5,262,619, 6,192,169, 6,374,045, 7,012,222; and PCT international publications WO 97/02054, WO 97/45008, and WO 98/57674; and European patent application EP 0 965 267.

PTC resistors, such as that used in the device of WO 2006/046209, typically have a generally flat, pill-like shape having a selected thickness. The PTC resistor must be firmly secured between two electrical contacts, thus completing a circuit that allows electrical current to flow through the PTC resistor, causing it to heat. A failure to secure the PTC resistor can lead to unreliable electrical contacts and therefore unreliable heating. Also, if the PTC resistor is held within a space larger than the resistor, the same means that secure it to ensure good electrical contact may also function to prevent the resistor's movement should the device within which it is located be shaken, dropped, or the like. PTC resistors are fairly delicate and subject to breakage.

Also, in many devices, the electrical terminal/contact retainer system which has a pressure contact with the PTC resistor is a stamped part. As a result, there will occasionally be sharp edges, such as stamping burrs, formed on the electric contact. When these sharp edges come into contact with the fragile PTC resistor, there can be an incidence of cracking of the PTC resistor over time, particularly as it heats and cools through use.

Therefore, the art is continually challenged to create ways to secure PTC resistors by retainer systems and assembly techniques that successfully firmly hold the resistors, with good electrical contact, but with carefully controlled pressures and without sharp edges that could initiate cracking of the PTC resistor. Accordingly, the present invention is directed to meeting these needs.

SUMMARY OF THE INVENTION

In one aspect, the invention provides a retainer system for retaining a positive temperature coefficient resistor in a housing shaft having a shaft side wall. The retainer system includes a base, a spring, and housing shaft engagement means. The spring is formed in and spaced apart from the base. The spring extends radially outwardly from a longitudinal axis of the base and the spring has a neck that curves radially backwardly, spaced apart from the base and toward the longitudinal axis of the base. The spring also has a contact surface presented outwardly, away from the base. The shaft engagement means are for engaging the housing shaft side wall and securing the base within the housing shaft at a desired distance from the resistor. The retainer system can be secured within the housing shaft with the spring flexed to a desired extent and with the contact surface urged against the resistor to retain the resistor in the housing shaft. Any sharp edges are away from the contact surface.

In one form, the spring of the retainer system has a movable foot attached to the base and the foot is generally parallel or coplanar with the base before flexing of the spring. The foot has a width and sides, and the width of the foot may be curved from side to side. The neck of the spring also has a width and sides, and a selected portion of the width of the neck may be curved from side to side. The base may have a central gauge hole. In one version of the retainer system, the shaft engagement means includes circumferentially spaced apart engagement members extending radially outwardly from the base for a distance sufficient to engage the housing shaft wall when the retainer system is inserted into the housing shaft. The retainer system may include a leg extending outwardly from the base, and the leg may include at least one tab for engaging an electrical lead.

In another aspect, the invention provides a heater including a housing, a shaft within the housing wherein the housing shaft has a shaft side wall that terminates in a closed shaft end wall, an electrical contact adjacent or contacting the shaft end wall, a positive temperature coefficient resistor located within the shaft and in contact with the electrical contact, and a retainer system retaining the resistor in the shaft and urging the resistor against the electrical contact. The retainer system includes a base, a spring, and shaft engagement means. The spring is formed in and spaced apart from the base. The spring extends radially outwardly from a longitudinal axis of the base and the spring has a neck that curves radially backwardly, spaced apart from the base and toward the longitudinal axis of the base. The spring also has a contact surface presented outwardly, away from the base. The shaft engagement means are for engaging the housing shaft side wall and securing the base within the housing shaft at a desired distance from the resistor. The retainer system can be secured within the housing shaft with the spring flexed to a desired extent and with the contact surface urged against the resistor to retain the resistor in the housing shaft.

In one form, the spring of the retainer system has a movable foot attached to the base and the foot is generally parallel or coplanar with the base before flexing of the spring. The foot has a width and sides, and the width of the foot may be curved from side to side. The neck of the spring also has a width and sides, and a selected portion of the width of the neck may be curved from side to side. The base may have a gauge hole. In one version of the retainer system, the shaft engagement means includes circumferentially spaced apart engagement members extending radially outwardly from the base for a distance sufficient to engage the housing shaft wall when the retainer system is inserted into the housing shaft. The retainer system may include a leg extending outwardly from the base, and the leg may include at least one tab for engaging an electrical lead of the heater.

In yet another aspect, the invention provides a method of manufacturing a heater having a housing, a shaft within the housing wherein the housing shaft has a shaft side wall terminating in a housing shaft end wall, an electrical contact, a positive temperature coefficient resistor, and a retainer system. The retainer system includes a base, a spring, and shaft engagement means. The spring is formed in and spaced apart from the base, and the spring extends radially outwardly from a longitudinal axis of the base. The spring also has a neck curving radially backwardly, spaced apart from base and toward the longitudinal axis of the base. The spring also has a contact surface presented outwardly, away from the base. The shaft engagement means are for engaging the housing shaft wall and securing the base within the housing shaft at a desired distance from the resistor. There is also an opening in the base providing a gauge hole therethrough. The retainer system may include a leg extending outwardly from the base, and the leg may include at least one tab for engaging an electrical lead of the heater.

In the method, the electrical contact is inserted in the shaft adjacent or contacting the shaft end wall, and then the resistor is inserted in the housing shaft, adjacent the electrical contact. The retainer system is inserted in the housing shaft with the contact surface presented toward the resistor, and the retainer system is urged toward the resistor with a probe having a gauge member extending through the gauge hole. The retainer system is then moved toward the resistor until the gauge member contacts one of the resistor and the spring. This ensures a predictable and consistent flexing of the spring, resulting in a predictable and consistent pressure against the resistor and range of movement of the spring in response, for example, to expansion of the housing as it is heated. In one version of the method, the leg of the retainer system is bent toward the axis of the base for engaging the tab(s) of the leg with an electrical lead of the heater.

It should be appreciated that the retainer system can be manufactured by being punched out of sheet metal with the punch approaching from what will become the side of the base opposite to the final location of the spring. The spring, after the punching step but before final manufacturing steps, initially extends outwardly from the base in the same plane as the base. Any burr or other sharp remnants of the punching process will extend away from the plane of the base, in the direction opposite to the direction of travel of the punch. The spring is then bent back over the base to assume its final shape and may be so bent that any burr or other sharp remnants of the spring's creation will project back toward the base and away from the resistor, when the retainer system is in use. Thus, the use of the retainer system of the present invention keeps any edge of the retainer system which might have burrs or other sharp remnants from formation, away from the fragile PTC resistor. Hence, the risk of such defects causing PTC resistor cracks over time is eliminated.

Further, the combination of such a retainer system with a spring contact surface and engagement members renders the retainer system suitable to optimize pressure against the PTC resistor while also positioning the retainer system relative to other assembly parts. Also, the use of the retainer system in assembly reduces costs associated with assembling the heater housing parts.

The spring of the retainer system allows for significant pressure to be exerted by the spring over an increased distance compared to other known contacts. One known heater housing is a high temperature plastic. It expands a bit as it heats. An advantage of the retainer system of the invention is that it can continue to exert adequate pressure on the side of a PTC resistor over an increased distance, thus remaining effective even as that expansion increases the distance between the retainer and the PTC resistor. Good pressure ensures electrical contact and avoids movement of the PTC resistor. But it also forces the PTC resistor firmly against the end wall of the housing shaft, accomplishing a better thermal transfer.

The foregoing and other advantages of the present invention will become apparent from the following description. In that description, reference will be made to the accompanying drawings which form a part thereof, and in which there is shown by way of illustration certain embodiments of the invention. These embodiments do not represent the full scope of the invention. Reference should therefore be made to the claims herein for interpreting the scope of the invention.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
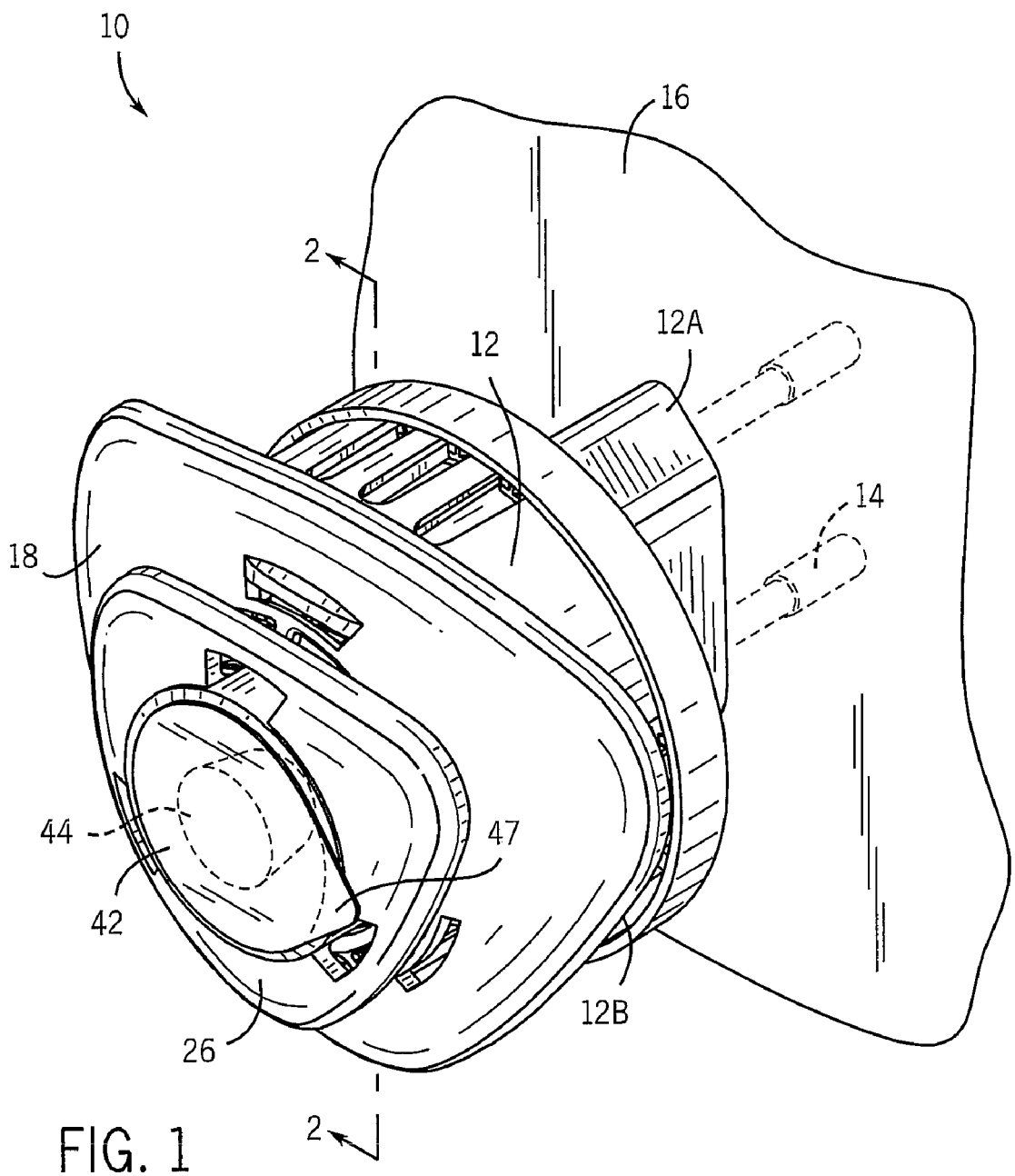
FIG. 1 is a frontal, right perspective view of an example air treatment device in which the retainer system of the present invention may be used, the air treatment device being plugged into a vertical wall.

As background, an example air treatment device 10 in which the retainer system of the present invention may be used will be described. Referring to FIG. 1, the air treatment device 10 has an outer housing 12 comprising a rear portion 12A and a frontal portion 12B. An electrical prong structure 14 is positioned in the housing 12, in the rear portion 12A, and has a rearward end extending rearwardly outwardly therefrom.

Figure 2:
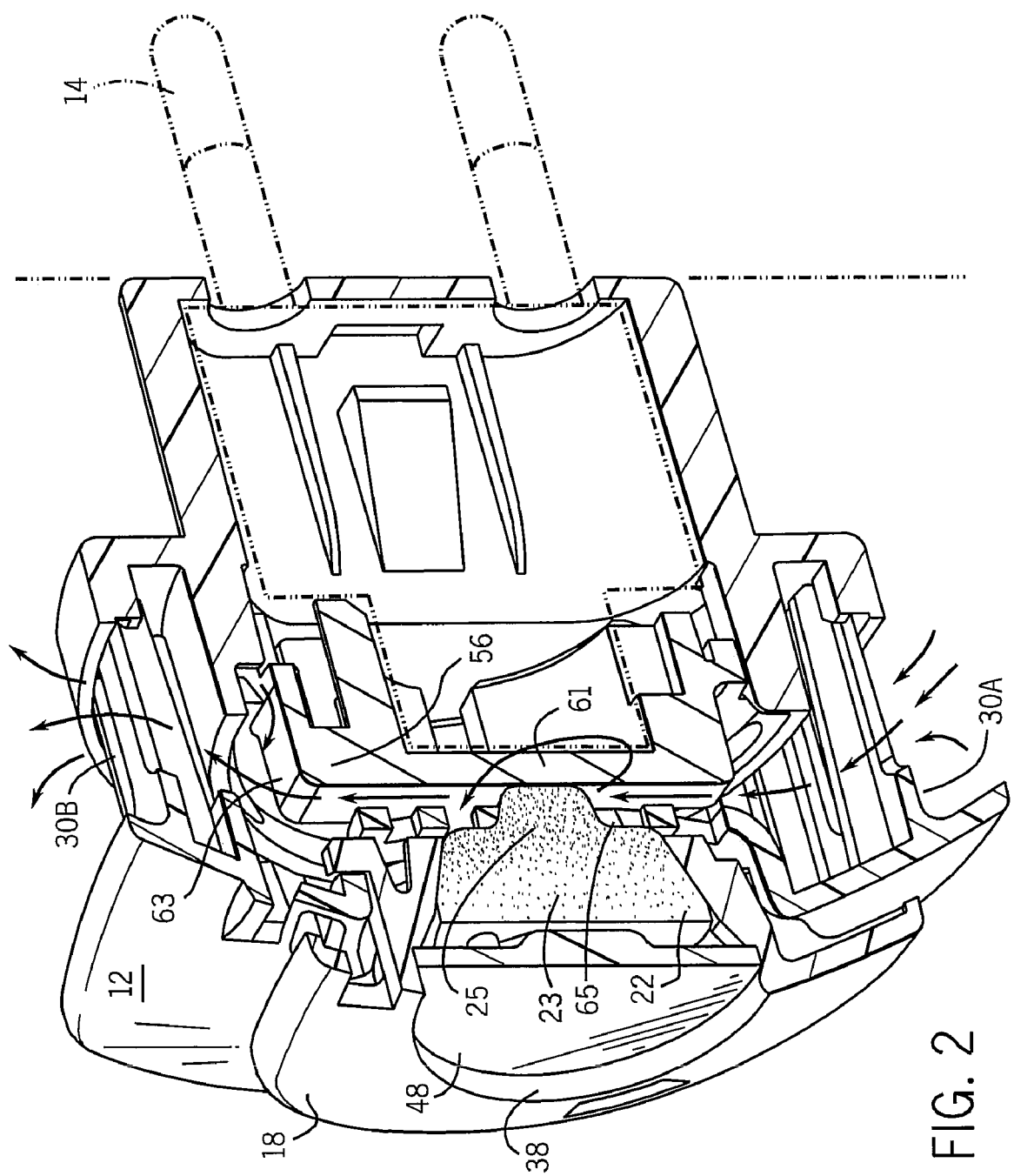
FIG. 2 is a sectional view taken along line 2-2 of FIG. 1, albeit with an indicator unit 26 removed.

There is also a cover unit 18 mounted to the frontal housing portion 12B. The cover unit 18 mounts a substrate 22 (see especially FIG. 2) such that the substrate 22 is essentially outwardly frontally covered, but is open towards the interior of the housing. In a particularly preferred version there is a separately installable indicator unit 26 removably mountable to the cover unit 18 so as to project outwardly and forwardly. The indicator unit 26 is preferably removable from the cover unit 18, and houses a separate indicator chemical in a cup-shaped structure 44, which may indicate to a user the amount of air treatment chemical remaining in the substrate 22. The indicator unit 26 may have a removable lid 42 with an easy-grab tab 47. The rear of the indicator unit 26 may extend into a well 38 formed in the cover unit to facilitate some heat transfer through wall 48 to the indicator unit.

Examples of a suitable substrate 22 include but are not limited to porous sand with a binder such as novolac resin, urethane resins or highly cross linked thermoplastics such as cross linked polyethylene. Particularly preferred sand substrates can be made in a fashion analogous to the sand wicks described in U.S. patent application publication 2005/0284952. Alternative substrates include other particulates such as metal, cellulose, and ceramic particulates. The air treatment chemical is preferably an insecticide, fragrance and/or disinfectant. In some cases more than one air treatment chemical may be used alone or in combination in the substrate 22.

The device 10 is most preferably plugged into an electric socket on a vertical wall 16. The directional terms in this patent are used with that type of installation in mind. However, appropriate electric sockets on horizontal or other surfaces may also be used to provide power. Thus, the terms such as "front", "rear", "upper", "lower", and "side" should be interpreted in an analogous manner when the devices are used for that type of installation.

The electrical prong structure 14 shown in the figures are merely for purposes of example. Cylindrical prongs of this type are suitable for linking to electric power in some countries. However, in other countries blade prongs, or mixtures of blades, cylinders and other shaped prong elements will be used to supply the linkage to the available power (as is well recognized in the art).

The frontal housing 12 has a series of elongated vents 30A, 30B on its upper and lower sides. The vents 30A form an inlet part of an air pathway, by allowing air from the environment to enter. Air then passes as shown by the arrows in FIG. 2.

Note that the heater 56 is in the form of a table having a frontal facing wall 61 and a side wall structure 63. Heat can radiate towards the substrate 22, and also sideways around the table. Thus, air entering the vents 30A will heat up very quickly and efficiently.

Note also that the nose projection 25 on the substrate 22 can be in direct contact with the facing wall 61. This permits direct heat transfer. Nevertheless, additional heat can be applied along the sides of the nose as the somewhat heated air passes between the wall 65 of the substrate that faces the table and the facing wall 61.

This is particularly effective in causing a very fast burst of insecticide or other air treatment chemical when the device is first turned on. Hence, a room can be rendered adequately treated quite quickly. Also, where the substrate 22 is of the type that wicks the air treatment chemical towards the wall 65, the burst can be repeated after the device has been shut off for a day and then turned on again.

After the air treatment chemical has been released into the air adjacent facing wall 61, it will pass generally transversely along the facing wall 61 until it exits outlet vent 30B. This then treats the surrounding environmental air with the air treatment chemical.

While the preferred substrate shape is a substrate having a forward frustum shaped section 23 and a rearward projecting nose 25, other shapes can be used, with or without a projecting portion. The substrate 22 is preferably completely impregnated with a volatile air treatment chemical capable of being dispensed from the substrate 22 when the substrate 22 is heated. However, as an alternative to being completely impregnated with the air treatment chemical, the substrate 22 may instead be only partially impregnated or just coated with the air treatment chemical.

The housing 12 of the overall device 10 encloses the table-shaped heater 56 with a sufficient insulation gap to the outer housing wall to prevent the side wall from heating too much.

Figure 4A:
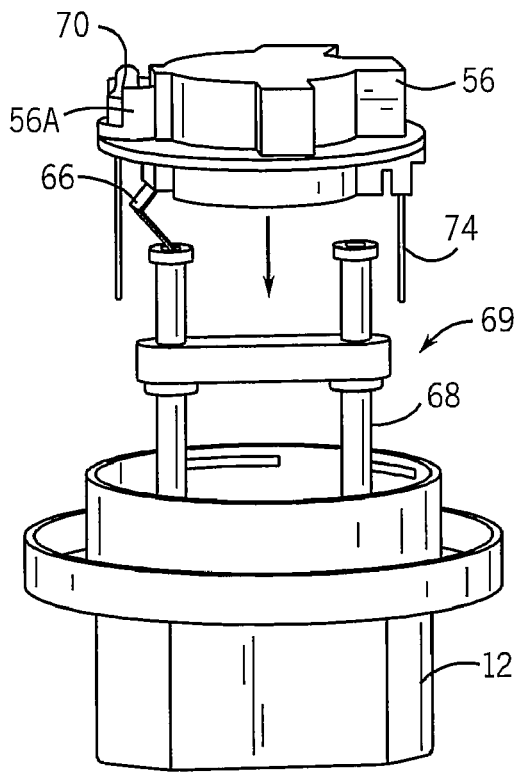
FIGS. 4A-4C illustrate a portion of an example method of assembly of a housing, an electrical plug structure, and a heater of the device of FIG. 1.
Figure 4B:
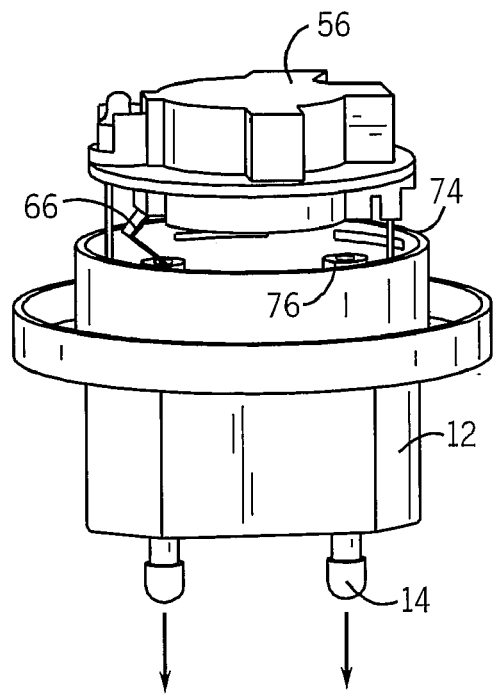
Figure 4C:
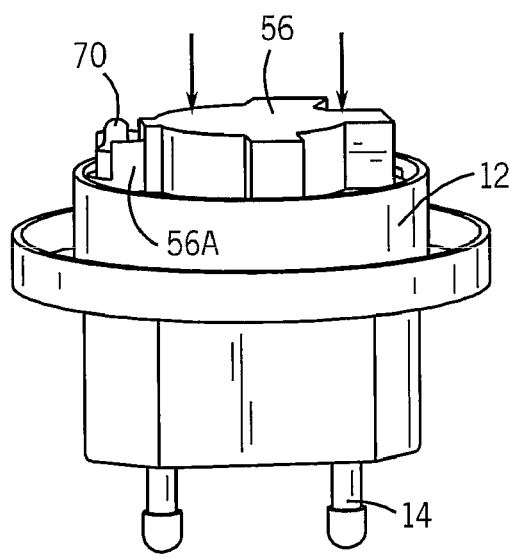
Figure 4D:
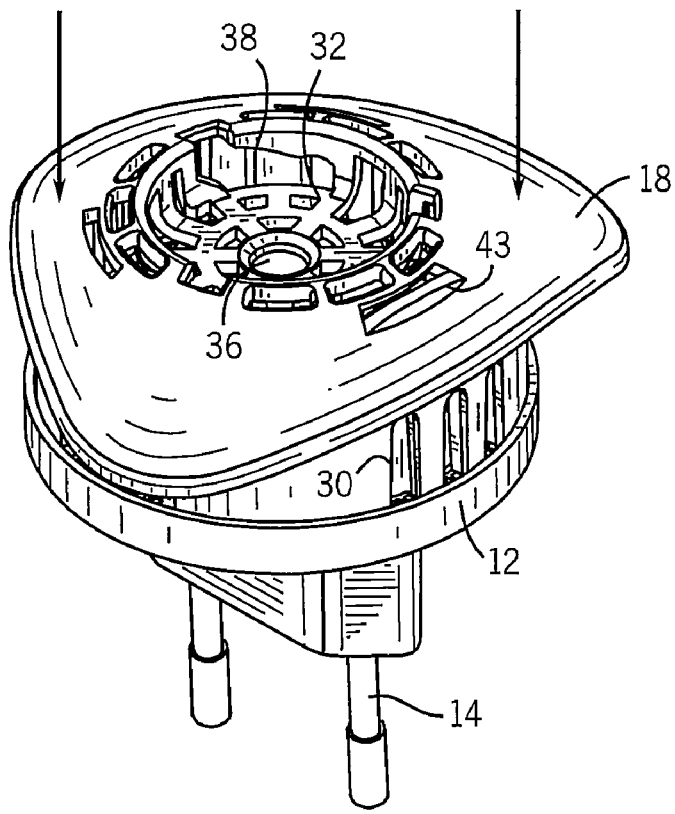
FIGS. 4D and 4E illustrate further steps of assembly of a device of FIG. 1.
Figure 4E:
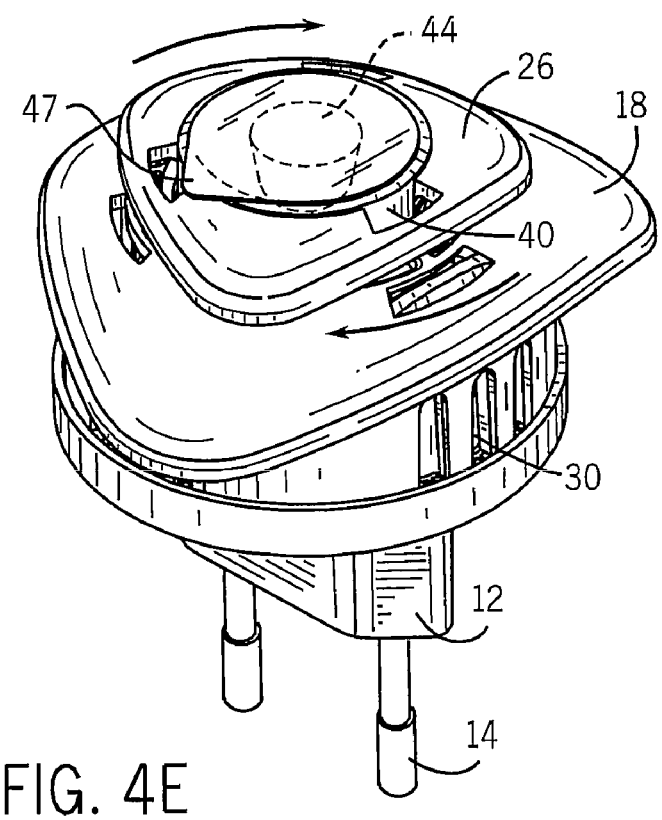
Figure 5:
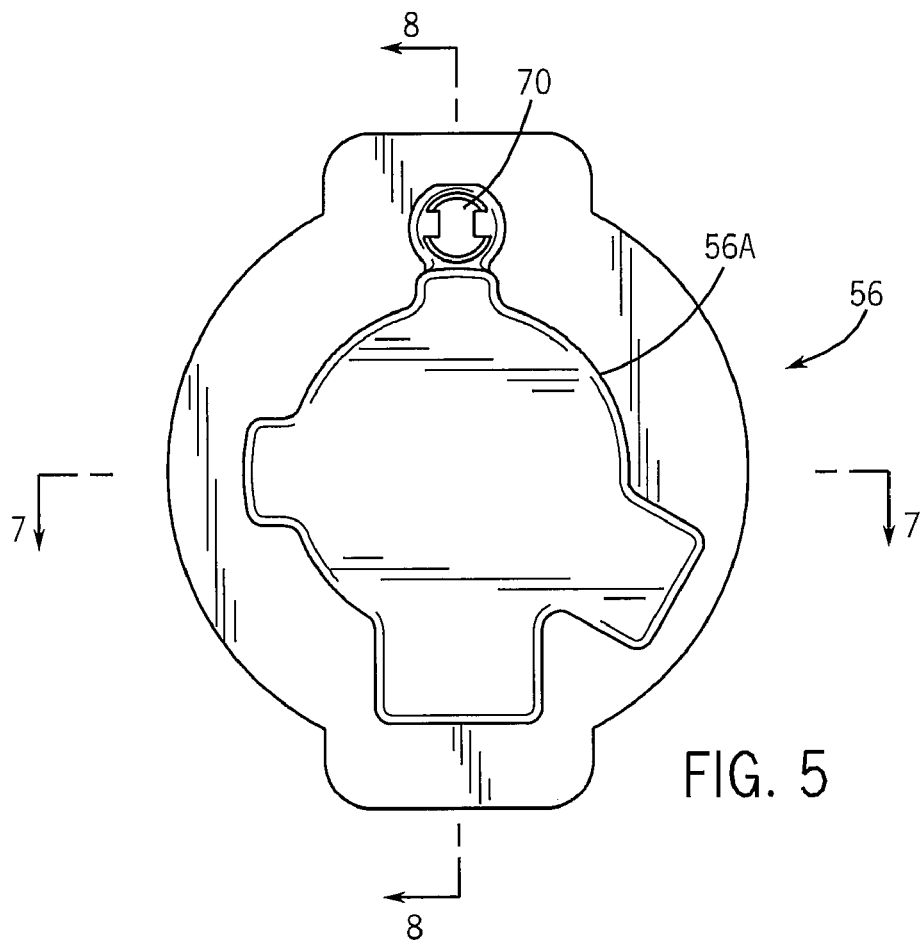
FIG. 5 is a top plan view of a heater of the device of FIG. 1.

The heater is preferably activated by inserting the rearward end of the electrical prong structure 14 into an outlet. Heat from the heater 56 may also be permitted to pass against other surfaces of the cover unit 18 through a series of openings 32 and 36 (see FIG. 4D). Note that wall 48 effectively closes off air dispensing through the front of the device.

Figure 3:
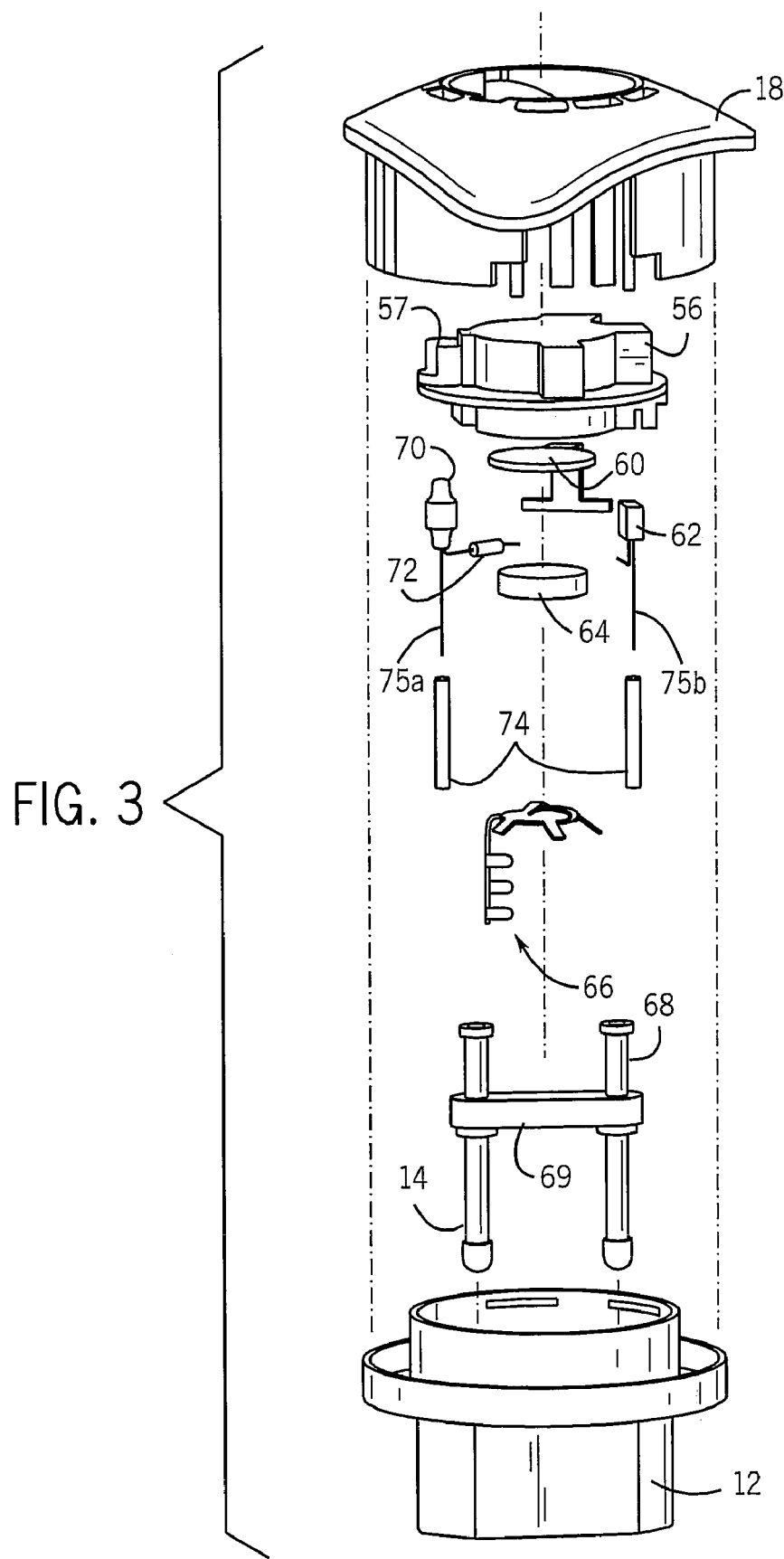
FIG. 3 is an exploded view of the FIG. 2 device.

Referring next to FIG. 3, from top to bottom (forward to rear in the installed device), the device 10 has a removable cover unit 18 (shown here without the indicator unit 26) which, lockingly engages with the heater 56, in a subassembly, after positioning the substrate in the cover unit. This can be achieved with a snap fit connection, or by a bayonet connection, or by other means.

A heater housing 56A is linked to a metallic electrical contact plate 60, a thermal cutoff ("TCO") 62, a positive temperature coefficient resistor 64 ("PTC resistor"), a neon in-use light 70, and a resistor 72, all of which telescopingly, matingly engage with the underside of the heater housing 56A. The TCO 62 and light 70 each have an end which matingly engage with corresponding sleeves 74, which in turn snap into corresponding holes in the housing 12. Electrical leads 75a and 75b run through the sleeves 74. A retainer system 66 according to the invention is inserted between the PTC resistor 62 and one of two plug decks 68 forming a pin bridge 69. In turn, the pin bridge 69 preferably snaps into the housing 12, thereby completing the device 10. The heater housing 56A may be made of any material suitable for the environment (e.g. heat resistant metals, plastics and the like). While the heater can be of many forms, a resistance heater is preferred. Once the device is plugged in, the electric current moves through the electrical prong structure 14 to drive the heater 56 and the on light 70. Overheating is prevented by the TCO 62.

Referring next to FIGS. 4A-4E, the telescopic, snap-fit assembly method of the device 10 is depicted. In the most preferred form each piece of the device 10 preferably telescopically fits together, and in some cases the parts snap fit together to lock the assembly together. In use, the on light 70 telescopingly engages an opening 57 within the heater housing 56A configured to accommodate the on light 70. When the light 70 is properly positioned in the opening 57, the light 70 snaps into position, thus securing the light 70 to the heater housing 56A. When the light 70 is snapped in place, the retainer system 66 is telescopingly inserted into a plug deck 68 of the pin bridge 69 and snapped in place. At the same time, the pin bridge 69 is inserted into the housing 12 and snapped in place.

The electrical prong structure 14 includes a bridge 69. The electrical prong structure is pulled through the rearward end of the housing 12 until the prongs snap in place (see FIG. 4B). This pulls the heater housing 56A over the contact plate 60, TCO 62, PTC resistor 64, and resistor 72. The heater housing 56A is preferably pushed down towards the housing 12, past retaining beads (not shown) until the heater housing 56A snaps into place in the housing 12 (see FIG. 4C).

Once the heater housing 56A is secured in the housing 12, the cover unit 18 (with the substrate 22 included) is preferably inserted into corresponding openings on the housing (not shown) by pressing firmly downward until the cover unit 18 snaps into place. Finally, an optional indicator unit 26 or other decorative plate (not shown) may be screwed into place on the front of the cover unit 18 by engaging the legs 40 of the indicator unit with corresponding openings 43 defined by the cover unit 18. Similarly, legs (not shown) of the cover unit 18 permit a quick, snap-fit attachment to the housing 12 via corresponding grooves 50 in the housing 12. See e.g. FIG. 4E.

Having described an example air treatment device 10 in which the retainer system 66 of the present invention may be used, the retainer system 66 will be described in further detail with reference to FIGS. 5-11. Looking first at FIGS. 5-8, the heater 56 includes heater housing 56A as described above. The heater housing 56A has a shaft side wall 81 that defines a housing shaft 82 in the heater housing 56A. The shaft side wall 81 terminates at a housing shaft end wall 83. The shaft side wall 81 could be a single circular wall or could include a number of separate walls that form the entire shaft side wall 81.

Figure 9:
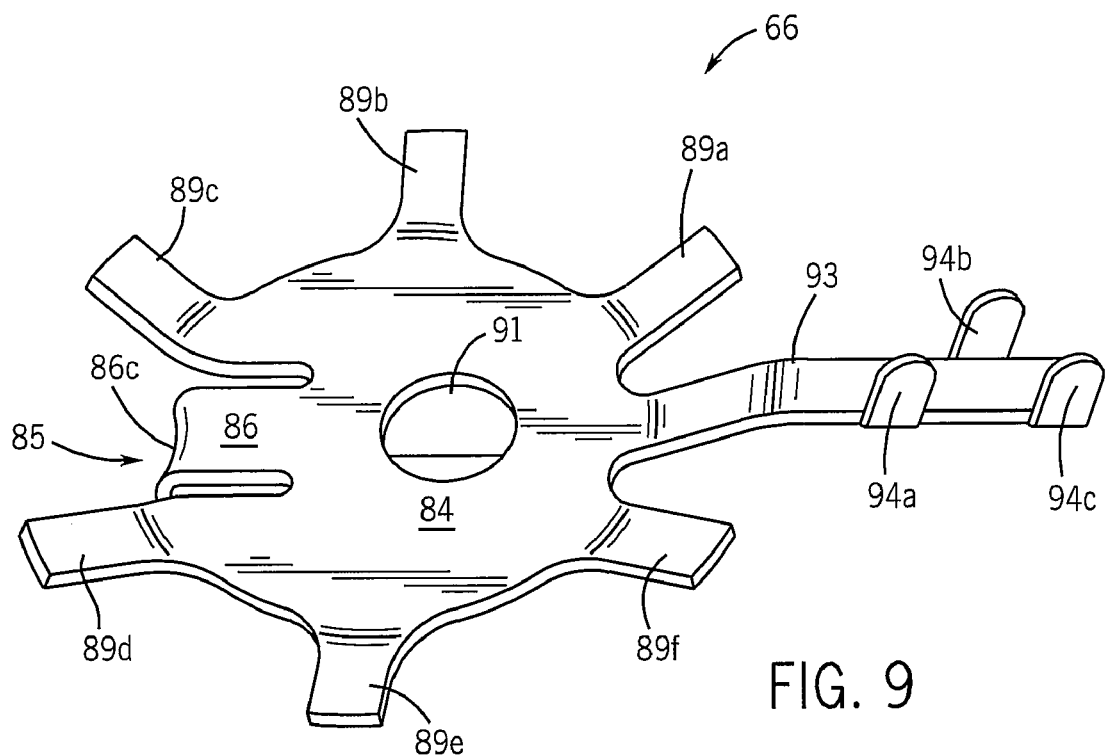
FIG. 9 is a top perspective view of a retainer system according to the invention.
Figure 10:
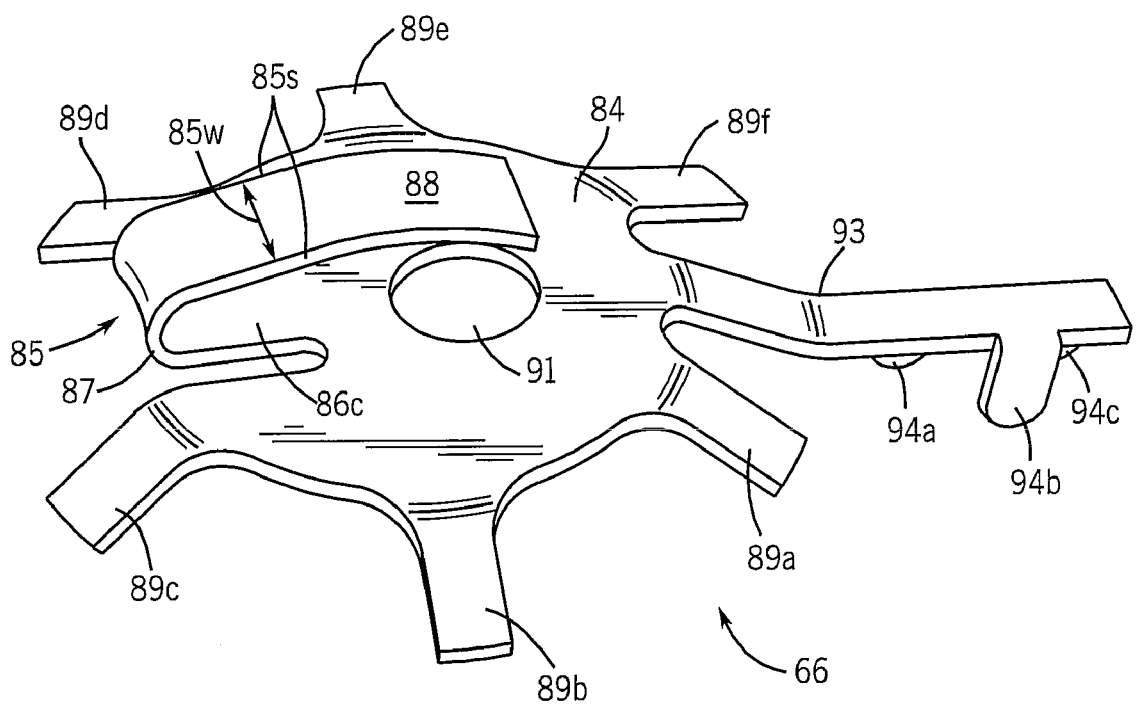
FIG. 10 is bottom perspective view of the retainer system of FIG. 9.
Figure 11:
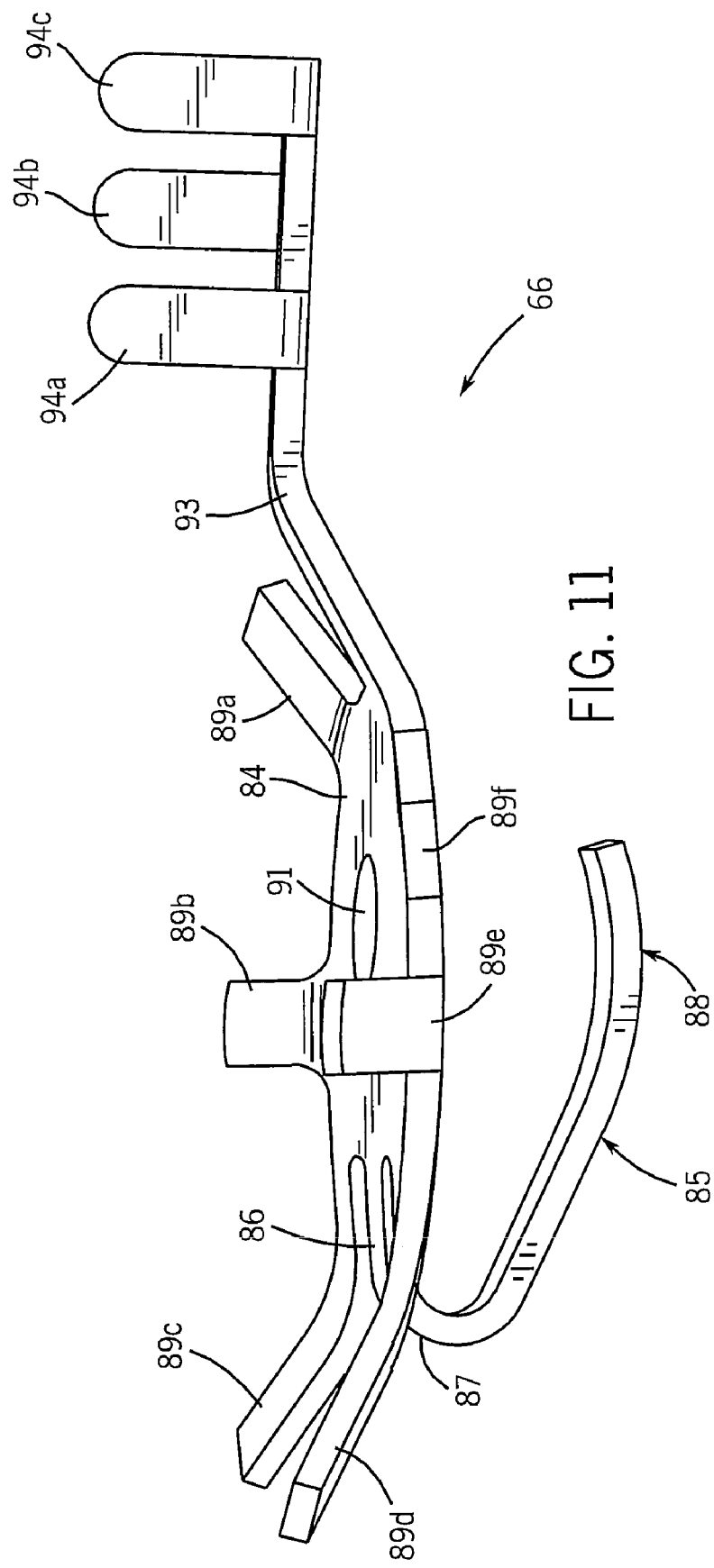
FIG. 11 is a side view of the retainer system of FIG. 9.

Turning now to FIGS. 9-11, the retainer system 66 is shown in its configuration before assembly into the heater 56. The retainer system 66 may be formed from any conductive material. In one preferred form, the retainer system 66 is formed from American Iron and Steel Institute (AISI) Type 304 stainless steel. The retainer system 66 has a generally flat base 84 having a longitudinal axis A (see FIG. 7). A spring 85 is formed in and rises above the base 84 (in the view of FIG. 10). The spring 85 has a width 85w and opposed sides 85s. The spring 85 also has foot 86 attached to the base 84. The foot 86 is generally parallel or coplanar with the base 84 before flexing of the spring. The width of the foot 86 is curved from side to side (e.g., upwardly curved from side to side in FIG. 10). The spring 85 extends radially outwardly from the longitudinal axis A of the base 84 and has a neck 87 that curves radially backwardly from the foot 86 spaced apart from the base 84 (e.g., above the base 84 in FIG. 10) and toward the longitudinal axis A. The spring 85 also has a contact surface 88 presented outwardly, away from the base 84. In FIG. 10, the contact surface 88 is generally horizontal. Any burrs on the spring 85 will be on a side of the spring 85 opposite the contact surface 88. Therefore, the burrs will be kept away from the PTC resistor 64. Hence, the risk of such burrs causing PTC resistor cracks over time is eliminated. Also, the longitudinal length of the contact surface 88 of the spring 85 may exceed half the diameter of the base 84 thereby allowing the spring 85 of the retainer system 66 to provide for significant pressure to be exerted by the spring 85 over an increased distance on the PTC resistor 64 compared to other known retainer systems.

The spring 85 also has housing shaft engagement means for engaging the housing shaft wall 81 and securing the base 84 within the housing shaft 82 at a desired distance from the PTC resistor 64. The preferred housing shaft engagement means of the retainer system 66 includes resilient circumferentially spaced apart engagement members 89a, 89b, 89c, 89d, 89e and 89f that extend radially outwardly from the base 84 for a distance sufficient to engage the shaft wall 81 when the retainer system 66 is inserted into the housing shaft 82. While the engagement members 89a, 89b, 89c, 89d, 89e and 89f are generally rectangular in the embodiment shown in FIGS. 9-11, other shapes (e.g., triangular, oval) would be suitable for engagement members 89a, 89b, 89c, 89d, 89e and 89f. Also, other numbers of engagement members would be suitable. While the use of such engagement members is preferred, it will be apparent that alternative housing shaft engagement means are also possible, including a separate ring or similar structure pressure fit into the housing shaft 82 behind the base 84, threads or other similar structures to receive cooperating structures extending from the base or from a separate ring or the like, or one or more clamps fastened to the heater at any convenient location. None of these alternatives are shown but, together with other functionally corresponding structures and techniques, will be easily understood by those skilled in the art.

The retainer system 66 has an opening in the base 84 providing a gauge hole 91 through the base 84. Also, a generally rectangular leg 93 extends radially outwardly from the base 84. The leg 93 has three tabs 94a, 94b, 94c that extend away from the sides of the leg 93 at a distal end of the leg 93. The tabs 94a, 94b, 94c are for engaging an electrical lead as described below.

Figure 7:
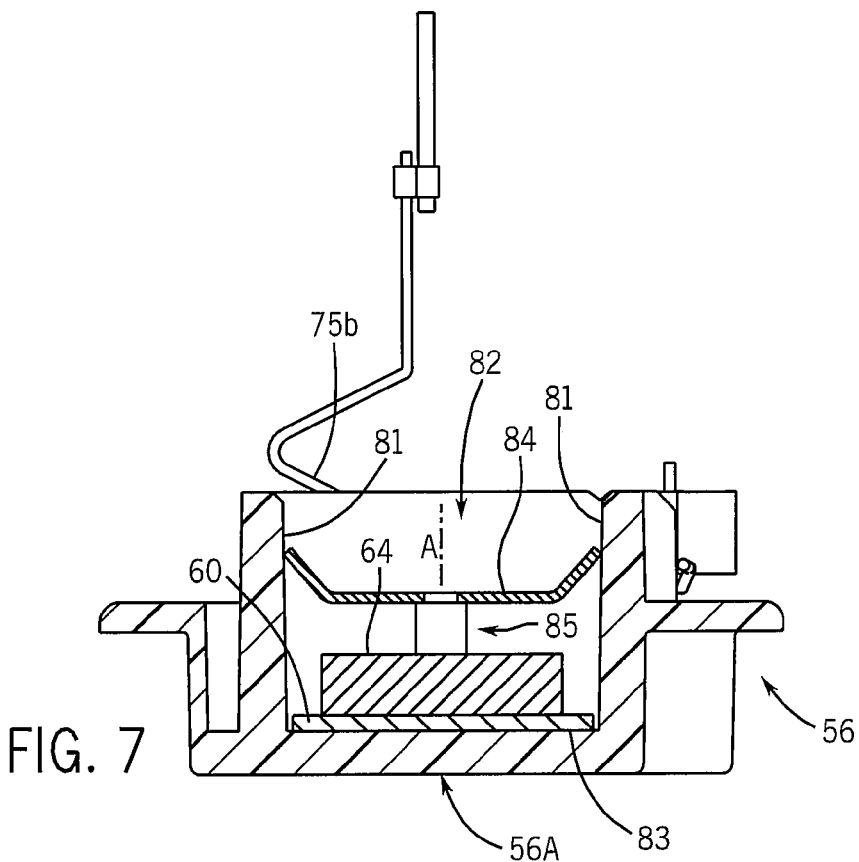
FIG. 7 is a sectional view taken along line 7-7 of FIG. 5.
Figure 8:
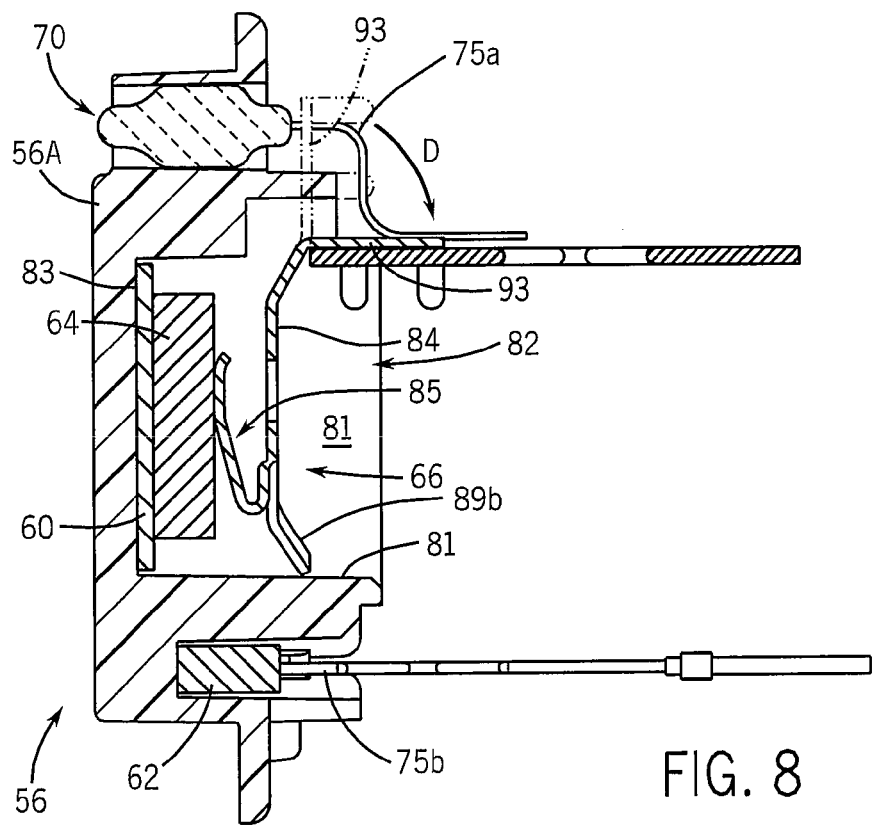
FIG. 8 is a sectional view taken along line 8-8 of FIG. 5.

An example method for using the retainer system 66 in assembly of a heater 56 can be explained with reference to FIGS. 7 and 8. First, a heater housing 56A is placed on a generally flat surface (not shown) such as a conveyer belt or worktable with the housing shaft 82 opening upward as shown in FIG. 7. The electrical contact plate 60 is then inserted in the housing shaft 82 adjacent, and typically in contact with, the housing shaft end wall 83. The PTC resistor 64 is then inserted in the housing shaft 82 adjacent the electrical contact plate 60. The retainer system 66 is then inserted in the housing shaft 82 with the contact surface 88 of the spring 85 presented toward the PTC resistor 64. A probe with a gauge member (not shown) is inserted in the gauge hole 91 of the base 84, and the probe urges the retainer system 66 toward the PTC resistor 64 with the probe extending through the gauge hole 91. The retainer system 66 is moved toward the PTC resistor 64 until the gauge member of the probe contacts either the PTC resistor 64 or the spring 85. Whether or not the gauge member of the probe contacts the PTC resistor 64 or the spring 85 is determined by the positioning of the spring 85 relative to the gauge hole 91.

The gauge member of the probe can include a suitable pressure sensor such as a transducer so that each time a retainer system 66 is installed in a housing shaft 82, the retainer system 66 is moved toward the PTC resistor 64 until the pressure sensor of the gauge member of the probe senses a predetermined pressure when the pressure sensor contacts either the PTC resistor 64 or the spring 85. By removing the probe each time when the predetermined pressure is reached, uniform placement of the retainer system 66 in the housing shaft 82 can be achieved. Thus, the assembly method with the probe provides an assembly technique that firmly holds the PTC resistor 64, with good electrical contact and with carefully controlled pressures.

Figure 6:
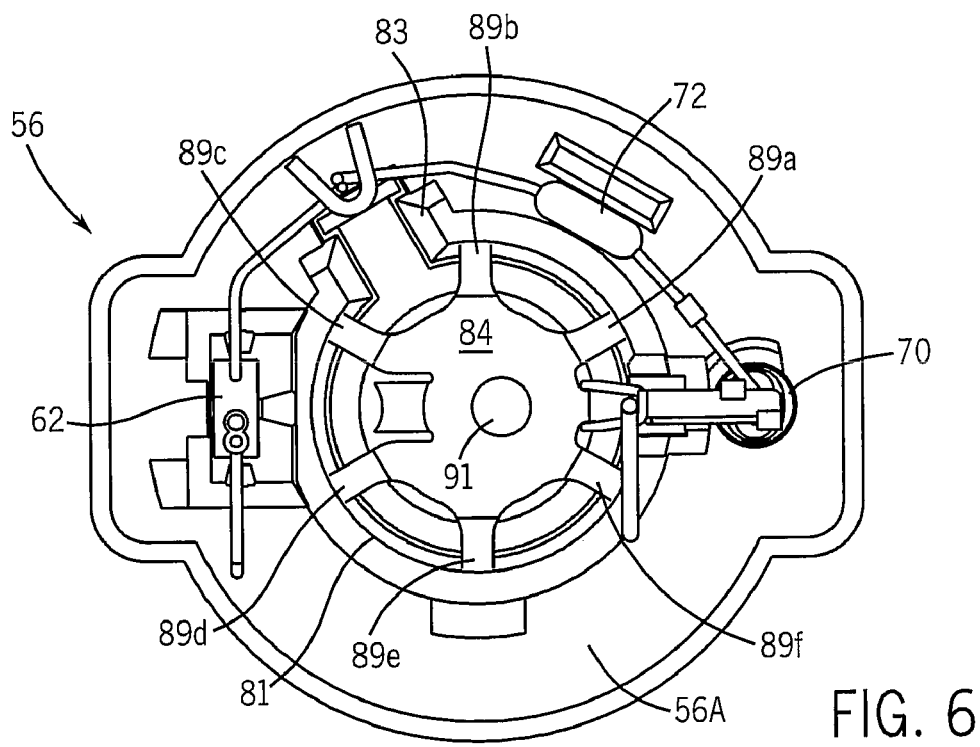
FIG. 6 is a bottom plan view of the heater of FIG. 5 showing a retainer system according to the invention.

During positioning of the retainer system 66 in the housing shaft 82, the resilient engagement members 89a, 89b, 89c, 89d, 89e and 89f engage the shaft wall 81 as shown in FIG. 6 thereby retaining the PTC resistor 64 and the electrical contact plate 60 in the housing shaft. Also, during or after positioning of the retainer system 66 in the housing shaft 82, the leg 93 of the retainer system 66 is bent in direction D of FIG. 8, and the three tabs 94a, 94b, 94c are crimped to engage the lead 75a. As a result, electrical current can flow to the light 70 and to the retainer system 66 where the current continues on to the PTC resistor 64, to the electrical contact plate 60 and back to the lead 75b.

While this invention has been described with reference to what are currently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

INDUSTRIAL APPLICABILITY

The retainer system of the invention relates to electrical heater devices that employ positive temperature coefficient resistors, and to the means and methods of securing positive temperature coefficient resistors within the housings of such electrical heater devices.

What is claimed is:

1. A retainer system usable in combination with a positive temperature coefficient resistor in a housing shaft having a shaft side wall, the retainer system being of a type suitable to be secured within the shaft with a spring portion of the retainer system flexed to a desired extent and with a contact surface of the retainer system being urged against the resistor to retain the resistor in the shaft, the retainer system comprising:
   a) a base having a longitudinal axis,
   b) a spring, wherein the spring has a portion extending radially outwardly from the longitudinal axis of the base and has a neck adjacent a radially outward portion of the radially outwardly extending portion of the spring that curves radially backwardly toward the longitudinal axis, the spring also comprising a contact extending from the neck radially inwardly to the longitudinal axis, the contact having a contact surface presented outwardly, away from the base and extending to the longitudinal axis, and
   c) a plurality of shaft engaging members for engaging the shaft side wall and securing the base within the shaft at a desired distance from the resistor;
   wherein the spring extends from an outer perimeter of the base.

2. The retainer system of claim 1 wherein:
the spring has a movable foot attached to the base, the foot being generally parallel or coplanar with the base before flexing of the spring.

3. The retainer system of claim 2 wherein:
the foot has a width and sides, and the width of the foot is curved from side to side.

4. The retainer system of claim 1 wherein:
the neck has a width and sides, and
a selected portion of the width of the neck is curved from side to side.

5. The retainer system of claim 1 further comprising:
an opening in the base providing a gauge hole therethrough.

6. The retainer system of claim 1 wherein:
the plurality of shaft engagement members includes engagement members extending radially outwardly from the base for a distance sufficient to engage the shaft wall when the retainer system is inserted into the shaft.

7. The retainer system of claim 1 further comprising:
a leg extending outwardly from the base, the leg suitable for engaging an electrical lead.

8. The retainer system of claim 7 wherein:
the leg includes at least one tab for engaging the electrical lead.

9. A heater comprising a housing, a shaft within the housing, the shaft having a shaft side wall that terminates in a shaft end wall, an electrical contact adjacent the shaft end wall, a positive temperature coefficient resistor located within the shaft and in contact with the electrical contact, and a retainer system retaining the resistor in the shaft and urging the resistor against the electrical contact, the retainer system including
   a) a base having a longitudinal axis,
   b) a spring, wherein the spring has a portion extending radially outwardly from the longitudinal axis of the base and has a neck adjacent a radially outward portion of the radially outwardly extending portion of the spring that curves radially backwardly toward the longitudinal axis, the spring also comprising a contact extending from the neck radially inwardly to the longitudinal axis, the contact having a contact surface presented outwardly, away from the base and extending to the longitudinal axis, and
   wherein the contact is configured such that any burr on the contact will project away from the resistor and towards the base when the retainer system is in use, and
   c) a plurality of shaft engagement members for engaging the shaft side wall and securing the base within the shaft at a desired distance from the resistor,
   whereby the retainer system is secured within the shaft with the spring flexed to a desired extent and with the contact surface urged against the resistor to retain the resistor in the shaft;
   wherein the spring extends from an outer perimeter of the base.

10. The heater of claim 9 wherein:
the spring has a movable foot attached to the base, the foot being generally parallel or coplanar with the base before flexing of the spring.

11. The heater of claim 9 wherein:
the foot has a width and sides, and the width of the foot is curved from side to side.

12. The heater of claim 9 wherein:
the neck has a width and sides, and
a selected portion of the width of the neck is curved from side to side.

13. The heater of claim 9 further comprising:
an opening in the base providing a gauge hole therethrough.

14. The heater of claim 9 wherein:
the plurality of engagement members includes engagement members extending radially outwardly from the base for a distance sufficient to engage the shaft wall when the retainer system is inserted into the shaft.

15. The heater of claim 9 further comprising:
a leg extending outwardly from the base, the leg suitable for engaging an electrical lead of the heater.

16. The heater of claim 15 wherein:
the leg includes at least one tab for engaging the electrical lead.

* * * * *